(12) United States Patent
Lippert et al.

(10) Patent No.: US 7,883,469 B2
(45) Date of Patent: Feb. 8, 2011

(54) DEVICE FOR DETERMINING CARDIAC FUNCTION PARAMETERS

(75) Inventors: Michael Lippert, Ansbach (DE); Gerald Czygan, Buckenhof (DE); Stefan Paule, Drosendorf (DE)

(73) Assignee: Biotronik CRM Patent AG, Baar (CH)

( * ) Notice: Subject to any disclaimer, the term of this patent is extended or adjusted under 35 U.S.C. 154(b) by 740 days.

(21) Appl. No.: 11/517,155

(22) Filed: Sep. 7, 2006

(65) Prior Publication Data
US 2007/0055170 A1    Mar. 8, 2007

(30) Foreign Application Priority Data
Sep. 8, 2005    (DE) ................. 10 2005 042 923

(51) Int. Cl.
*A61B 5/0452* (2006.01)
(52) U.S. Cl. ................................... 600/481
(58) Field of Classification Search ............... 607/3, 607/9, 17, 18; 600/481, 547
See application file for complete search history.

(56) References Cited

U.S. PATENT DOCUMENTS

| 5,154,171 | A |   | 10/1992 | Chirife |   |
|---|---|---|---|---|---|
| 5,243,976 | A | * | 9/1993 | Ferek-Petric et al. | 607/6 |
| 7,010,347 | B2 | * | 3/2006 | Schecter | 607/17 |
| 2003/0163058 | A1 |   | 8/2003 | Osypka et al. |   |
| 2005/0203429 | A1 |   | 9/2005 | Judy |   |

FOREIGN PATENT DOCUMENTS

| DE | 41 11 505 | 10/1992 |
| DE | 44 47 447 | 7/1996 |
| DE | 103 61 143 | 3/2005 |
| EP | 05 83 499 | 8/1992 |
| EP | 1 348 463 | 10/2003 |
| EP | 1384 433 | 1/2004 |
| EP | 1 510 173 | 3/2005 |
| WO | WO 98/19737 | 5/1998 |
| WO | WO 03/022143 | 3/2003 |

OTHER PUBLICATIONS

Priority App German Search Report, Jun. 13, 2006.
Priority App European Search Report, Jan. 2, 2007.

* cited by examiner

*Primary Examiner*—George R Evanisko
*Assistant Examiner*—Michael D'Abreu
(74) *Attorney, Agent, or Firm*—ARC IP Law, PC; Joseph J. Mayo

(57) ABSTRACT

A device for detecting the state of a heart on the basis of intracardial impedance measurement. The device has an impedance measuring unit, which has electrical terminals, configured to be electrically connected or to be connected to electrodes for delivering and detecting a current or voltage, and is implemented to ascertain an impedance on the basis of the dimension of the delivered current or voltage and the voltage drop caused by the current or the current caused by the voltage, as well as an analysis unit, which is connected to the impedance measuring unit and is implemented to derive a cardiac function parameter from a time curve of the impedance ascertained using the impedance measuring unit. The analysis unit analyzes the impedance curve assigned to a diastole and derives a cardiac function parameter characterizing the behavior of a heart during the diastole (filling phase of the ventricle).

21 Claims, 6 Drawing Sheets

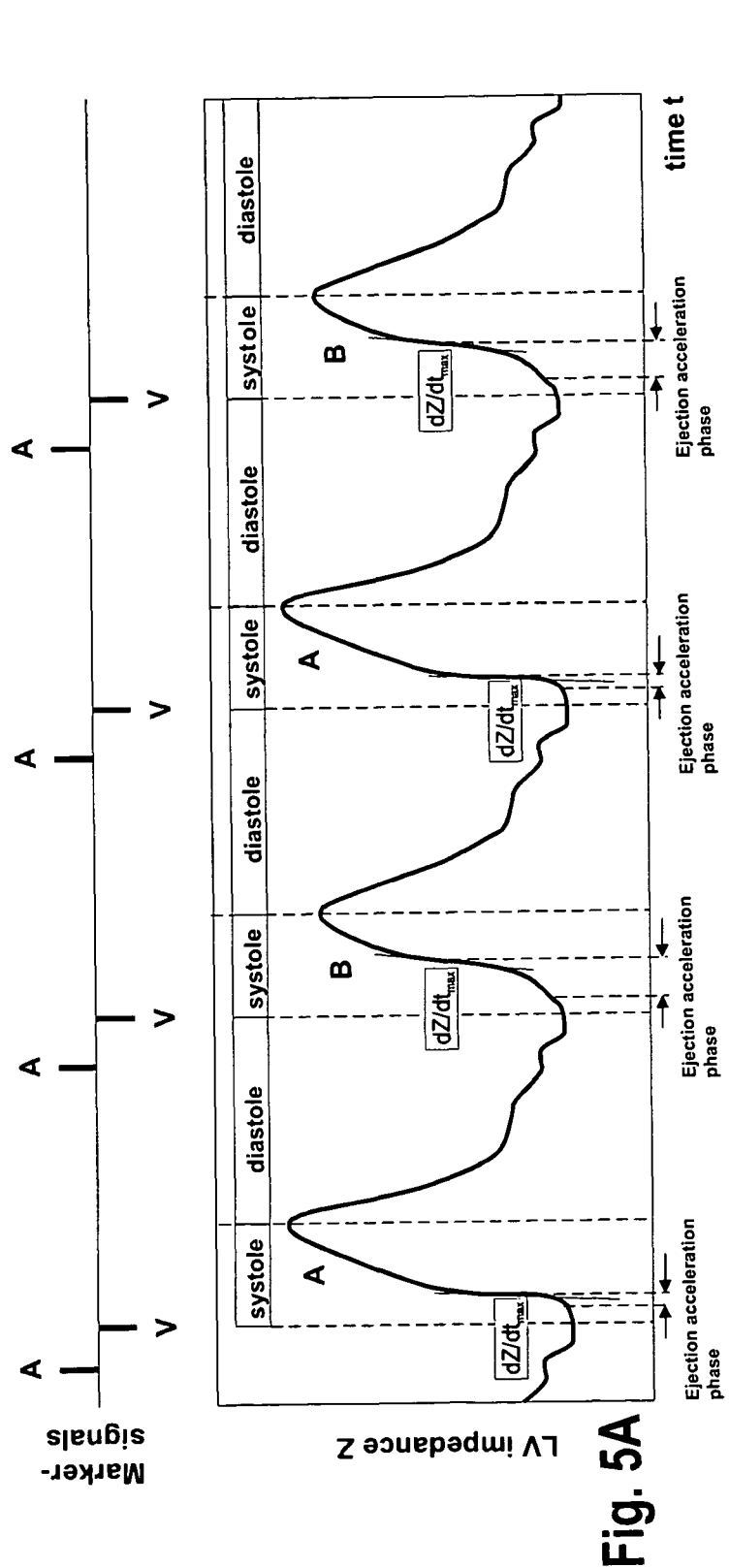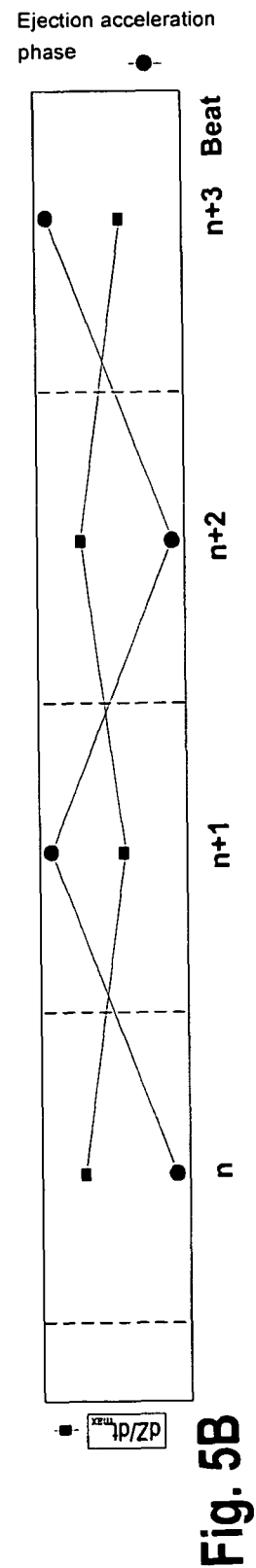
Fig. 5A
Fig. 5B

DEVICE FOR DETERMINING CARDIAC FUNCTION PARAMETERS

This application takes priority from German Patent Application DE 10 2005 042 923.8 filed 8 Sep. 2005, the specification of which is hereby incorporated herein by reference.

BACKGROUND OF THE INVENTION

1. Field of the Invention

The present invention relates to a device for determining cardiac function parameters by analyzing the intracardial impedance curve. For this purpose, the device has an impedance measuring unit which has electrical terminals to which electrodes for delivering a current and for detecting a voltage are to be connected or are permanently connected. Furthermore, the device has an analysis unit, which is connected to the impedance measuring unit and is implemented in such a way that it may derive a cardiac function parameter from a time curve of the impedance ascertained using the impedance measuring unit.

2. Description of the Related Art

A suitable impedance measuring system is known, for example, from German patent application DE 103 61 143. The impedance measuring system described therein is implemented to ascertain a cardiac function parameter proportional to the stroke volume of the heart from the intracardially detected impedance, namely the stroke impedance. The stroke volume describes the blood volume which is delivered by the heart during an ejection phase (systole). To ascertain the stroke impedance, the difference between the final diastolic impedance (at the end of the filling phase, i.e., diastole, of the heart) and the final systolic impedance at the end of the ejection phase (systole) is ascertained. Since the intracardially detected impedance is decisively determined by the good conductivity of the blood filling the heart, the impedance when the heart is maximally filled at the end of the diastole is less than when the ventricle is maximally contracted at the end of the systole. The final diastolic impedance is more or less coincident with the minimum of the impedance curve during a cardiac cycle, while the final systolic impedance is the maximum of the impedance curve during a cardiac cycle.

An impedance measuring system which is also preferred for the present invention is a quadropolar system as shown in FIG. 1a of DE 103 61 143 and described in the associated description. In a preferred impedance measuring system of this type, a pulsed constant current is delivered between the terminal for a right-ventricular tip electrode and the terminal for a right-ventricular ring electrode. In this preferred case, the voltage caused by the current is measured between the terminal for a left-ventricular tip electrode and the terminal for a left-ventricular ring electrode.

BRIEF SUMMARY OF THE INVENTION

The device according to the present invention relevant here is preferably a component of an electrostimulation device, which is implantable in the preferred case. Such an implantable electrostimulation device may be an implantable cardiac pacemaker or also an implantable cardioverter/defibrillator (ICD) or a combination of these implants, for example.

Proceeding from the known prior art, using the device claimed here, the object is to be achieved of allowing expanded and improved cardiac function analysis, which opens up expanded diagnostic and therapeutic capabilities as a result. A device suitable for this purpose is to be provided by the present invention.

This object is achieved according to the present invention in that the analysis unit of the above-mentioned device is implemented in such a way that, in operation, it analyzes the curve of the impedance signal assigned to a diastole and derives a value of a cardiac function parameter characterizing the behavior of a heart during the diastole.

The present invention is based on the recognition that valuable information about the behavior of the heart may also be inferred from the curve of the intracardial impedance during the diastole. The device according to the present invention accordingly has an analysis unit, which not only analyzes impedance values at the beginning of the diastole and at the end of the diastole, but rather also those impedance values which occur during the diastole to ascertain a cardiac function parameter. The device according to the present invention thus allows the detection of diastolic heart failure using intracardial impedance measurement for the first time. The detection of diastolic heart failure is thus also made possible for the first time using an implantable device, since a device of the type described here may be integrated easily into an implant.

Heart flaws impair the pumping power of a heart. Typically, both the systolic and also the diastolic functions of the heart are impaired. In some patients, primarily the relaxation process of the myocardium is impaired. Patients having a diastolic heart flaw display clinical symptoms which correspond to the symptoms occurring in systolic congestive heart failure (CHF: congestive heart failure), although the systolic function of the heart is normal or only slightly impaired. Diastolic heart flaws or diastolic heart failure may be caused by abnormal relaxation of the left ventricle or by increased passive rigidity of the myocardium or by other factors. The disturbed diastolic function impairs the filling of the ventricle during the passive diastolic phase. The passive filling of the ventricle, i.e., the ventricular filling phase because of the relaxation of the myocardium, provides the greatest contribution to the overall filling of the ventricle. The atrial contraction contributes only partially to the blood volume which flows in the ventricle. The impaired relaxation of the ventricle results in a compensatory increase of the filling pressure, which in turn results in an elevated left-atrial pressure and an elevated pulmonary capillary wedge pressure (PCWP). If only diastolic heart failure exists, the final diastolic volume is not increased and the systolic function remains normal. It is estimated that approximately a third of all CHF patients suffer from diastolic heart failure.

According to a preferred embodiment variation of the device according to the present invention, the analysis unit is implemented for the purpose of ascertaining the maximum impedance drop during the passive diastolic phase, i.e., the negative maximum of the gradient of the impedance curve. As the gradient of the impedance curve, in the scope of this application, the first derivative (slope) of the impedance curve according to time is identified as the first time derivative of the impedance curve. The negative maximum of the gradient of the impedance curve is a useful cardiac function parameter, because it is proportional to the early left-ventricular diastolic filling rate and characterizes the curve of the relaxation of the ventricular myocardium during the diastole. The absolute maximum of the (negative) first derivative of the impedance during the diastole LV $dZ/dt_{Min}$, i.e., during the reduction of the intracardial impedance, correlates (according to prior experimental investigations) with the corresponding gradient of the pressure curve LV $dp/dt_{Min}$ and also with the time constant of the pressure drop.

Under the assumption that the opening area of the mitral flap is constant, the negative slope (gradient) of the impedance curve is proportional to the flow speed of the blood flowing into the ventricle. Therefore, the pressure difference between the left ventricle and the left atrium may also be derived from the "negative" slope of the impedance curve on the basis of the Bernoulli equation, which is proportional to the square of the flow speed according to the pressure difference. The square of the maximum of this negative slope is thus proportional to the maximum pressure difference between the left ventricle and the left atrium.

Alternatively or additionally, the analysis unit is preferably implemented for the purpose of determining the period of time between the beginning of the impedance reduction and the following occurrence of the maximum negative gradient as a value of an alternative cardiac function parameter by analyzing the impedance curve. This cardiac function parameter is referred to in the following as the filling acceleration time. The beginning of the diastole, i.e., the beginning of the blood flow through the mitral flap, is thus determined by detecting the beginning of the impedance reduction. Alternatively, the instant of the occurrence of the impedance maximum within a cardiac cycle may also be determined.

The filling acceleration time thus determined is the period of time between the beginning of the blood flow through the mitral flap until reaching the maximum flow speed. This filling acceleration time correlates to the isovolumetric relaxation period and is a measure of the relaxation capability of the myocardium. In patients having diastolic heart failure, the filling acceleration time is lengthened.

In a variation which is also advantageous, the analysis unit is implemented to determine a filling deceleration time as a cardiac function parameter by analyzing the impedance curve. For this purpose, the analysis unit determines the period of time between the occurrence of the maximum negative gradient of the impedance curve and the apex of a parabolic approximation function of the impedance curve beginning with the occurrence of the maximum negative gradient of the impedance curve. Instead of determining the end of the filling deceleration time with the aid of a parabolic approximation function, the impedance curve may also be approximated by an exponential function, whose time constant $LV\tau(Z)$ represents the filling deceleration time, from the instant of the occurrence of the maximum negative gradient.

In a further advantageous variation, the analysis unit is implemented for the purpose of determining the ratio of the negative maximum of the gradient of the impedance curve between the beginning of the reduction of the impedance and a following atrial contraction to the negative maximum of the gradient of the impedance curve between this atrial contraction and the following further increase of the impedance curve by analyzing the impedance curve. In this way, the ratio of the maximum flow speed of the E wave, which describes the ventricular contribution to the filling of the left ventricle, and the A wave, which describes the atrial contribution to the filling of the left ventricle, is determined. The ratio thus determined is also referred to in the following as the $V_E/V_A$ ratio.

Finally, the duration of the diastole is a further cardiac function parameter which the analysis unit is preferably implemented to determine. In the preferred embodiment, the analysis unit determines this period of time in that the analysis unit first detects the beginning of the drop of the impedance curve after reaching the impedance maximum during a cardiac cycle and then detects the instant of the occurrence of the following impedance minimum.

In addition to the above-mentioned variations of the device having an analysis unit which is implemented to determine the cited values of cardiac function parameters, which characterize the diastole, in a preferred embodiment variation, the analysis unit may be implemented to determine additional values of those cardiac function parameters which describe the behavior of the heart during a systole. For this purpose, the analysis unit is implemented to determine the curve of the intracardial impedance during the systole, i.e., the ejection phase of the ventricle, which accompanies a contraction of the particular ventricle.

Such a systolic cardiac function parameter, which the analysis unit is preferably implemented to determine, is the positive maximum of the gradient of the impedance curve during the systole. During the systole, the impedance increases because blood is displaced out of the ventricle. The slope of the impedance curve, i.e., the first time derivative of the impedance curve during the ejection phase, corresponds to the rate of change of the left-ventricular volume. Under the assumption that the aortal flap has a constant cross-section during the ejection phase, the slope of the impedance is proportional to the outflow speed of the blood. This allows the pressure difference between the left ventricle and the aorta to be calculated from the slope of the impedance by considering the Bernoulli equation ($\Delta p \sim v2$). The square of the slope maximum is thus proportional to the maximum of the pressure difference between left ventricle and aorta.

In a further preferred variation, the analysis unit is implemented for the purpose of calculating the maximum of the slope of the gradient of the impedance curve, i.e., its second derivative according to time. In consideration of the Windkessel function of the aorta, the second time derivative of the impedance curve $LVd^2Z/dt^2$, multiplied by the first derivative $LVdZ/dt$, is a marker for the maximum left-ventricular pressure change $LVdp/dt_{Max}$, which is a measure of the contractility of the left ventricle. The property of the aorta section proximal to the heart of being able to elastically expand and contract again, and in this way smooth the pulsing of the blood flow somewhat, is referred to as the Windkessel function of the aorta.

According to a further preferred variation of the analysis unit, it is implemented to determine the period of time of the pre-ejection phase (PEP) as a cardiac function parameter by analyzing the impedance curve, in that the analysis unit determines the period of time between the electrical activation of the ventricular myocardium and the beginning of the impedance increase. The instant of the electrical activation of the ventricular myocardium may be determined by the analysis unit by detecting an R wave in the preferably intracardially recorded electrocardiogram (ECG) or by detecting the instant of delivery of a left-ventricular stimulation pulse. In order to determine the beginning of the impedance increase, the analysis unit may be implemented for the purpose of determining the instant at which the intracardial impedance exceeds a threshold value related to the impedance minimum.

An embodiment variation in which the analysis unit is implemented for the purpose of determining the period of time of the left-ventricular ejection time by analyzing the impedance curve, in that the analysis unit determines the period of time between the beginning of the impedance increase and the maximum of the impedance curve, is also preferred. The beginning of the impedance increase, i.e., the instant from which the intracardial impedance increases again in the course of time, corresponds to the opening of the aortal flap. The maximum of the impedance curve corresponds to the end of the ejection phase and the closing of the aortal flap.

An embodiment variation of the analysis unit in which the analysis unit is implemented for the purpose of determining the left-ventricular ejection acceleration time as a cardiac function parameter by analyzing the impedance curve is also preferred. For this purpose, the analysis unit is implemented to determine the period of time between the beginning of the impedance increase and the following occurrence of the maximum positive gradient of the impedance curve. The acceleration time thus determined is the time between the beginning of the ejection phase and the occurrence of the maximum flow speed of the blood.

In a similar way, the analysis unit may be implemented in a preferred variation for the purpose of determining the left-ventricular ejection deceleration time by analyzing the impedance curve. For this purpose, the analysis unit determines the period of time between the occurrence of the maximum positive gradient of the impedance curve during the systole and the following maximum of the impedance curve.

The ratio between the ejection acceleration time and the ejection deceleration time is influenced by a possible stenosis of the aorta: an increasing stenosis (constriction) of the aorta enlarges the proportion of the ejection acceleration time in the total duration of the systole.

In a further preferred embodiment variation of the device, the analysis unit is implemented for the purpose of determining the electromechanical deceleration time as the time difference between the electrical activation of the ventricle and the beginning of the impedance increase during the systolic phase. For this purpose the analysis unit is connected to an impedance measuring unit, which works together with impedance measuring electrodes in such a way that it detects a local right-ventricular or left-ventricular impedance signal, for example, using a unipolar or bipolar impedance measuring system in the right or left ventricle. Because the impedance used for determining the electromechanical deceleration time is the local right-ventricular or left-ventricular impedance, the electromechanical deceleration time differs from the duration of the pre-ejection period (PEP), which is determined on the basis of the impedance curve measured over the entire heart. The instant of the electrical activation of the particular ventricle may be determined by the analysis unit by analyzing an intracardial electrocardiogram in that the analysis unit determines the instant of the occurrence of an R wave in this electrocardiogram.

The device preferably has a memory in order to be able to record the previously described cardiac function parameters determined by analyzing the intracardial impedance curve for diagnostic purposes.

The memory preferably has at least two memory areas, of which a first memory area is provided for cardiac function parameter values which were detected during a phase of physical activity of the patient, and a second memory area, which is used for storing cardiac function parameter values which were detected during a rest phase of the patient. In order to be able to differentiate rest phases of the patient from activity phases, the device preferably has an activity detection unit. This may be coupled to a physiological sensor for determining the hemodynamic demand of the patient, for example, as is frequently used in rate-adaptive cardiac pacemakers for the purpose of adapting the stimulation rate. Such a physiological sensor may be an acceleration sensor, for example. The analysis unit is directly or indirectly connected to the activity detection unit and implemented for the purpose of storing the cardiac function parameter values determined by the analysis unit in the first or the second memory area of the memory, depending on the output signal of the activity detection unit.

It is advantageous if the analysis unit is also implemented to average cardiac function parameter values for a particular cardiac function parameter over time. For this purpose, the analysis unit makes use of cardiac function parameter values stored in the memory.

Furthermore, the analysis unit may be implemented to prepare histograms on the basis of the stored cardiac function parameter values. For this purpose, the device preferably has an activity detection unit, which is implemented for the purpose of differentiating multiple states of physical activity of different intensities. The memory has multiple memory areas in this embodiment variation and the analysis unit is implemented to store cardiac function parameter values in one of the memory areas as a function of the output signal of the activity detection unit depending on the intensity of the assigned physical activity.

Finally, the analysis unit may additionally be implemented to examine cardiac function parameter values of a cardiac function parameter as to whether the particular cardiac function parameter alternates from cardiac cycle to cardiac cycle (from heartbeat to heartbeat). Such an alternating behavior of a cardiac function parameter from beat to beat is also referred to in the following as alternation. A more detailed explanation of alternation is performed in connection with FIG. 5 in the following more detailed description of the present invention.

It is especially advantageous if the cardiac function parameter values ascertained by the analysis unit and stored in the memory, as well as values derived therefrom, such as mean values over time or histogram values, may be transmitted to a receiver outside the device using a telemetry unit of the device. For this purpose, a telemetry unit is preferably provided, which is connected to the memory and has at least one transmission unit for wireless transmission of data. A device of this type allows the various values stored in the memory to be transmitted to a central data processing unit, which may have a larger memory capacity and a larger computing capacity and is therefore capable of more extensive analysis of the data ascertained by the analysis unit.

BRIEF DESCRIPTION OF THE DRAWINGS

The present invention will now be explained in greater detail on the basis of an exemplary embodiment with reference to the figures. In the figures:

FIGS. 5A and 5B show a curve of the intracardial impedance over multiple cycles to illustrate an alternation.

DETAILED DESCRIPTION

Figure 1A:
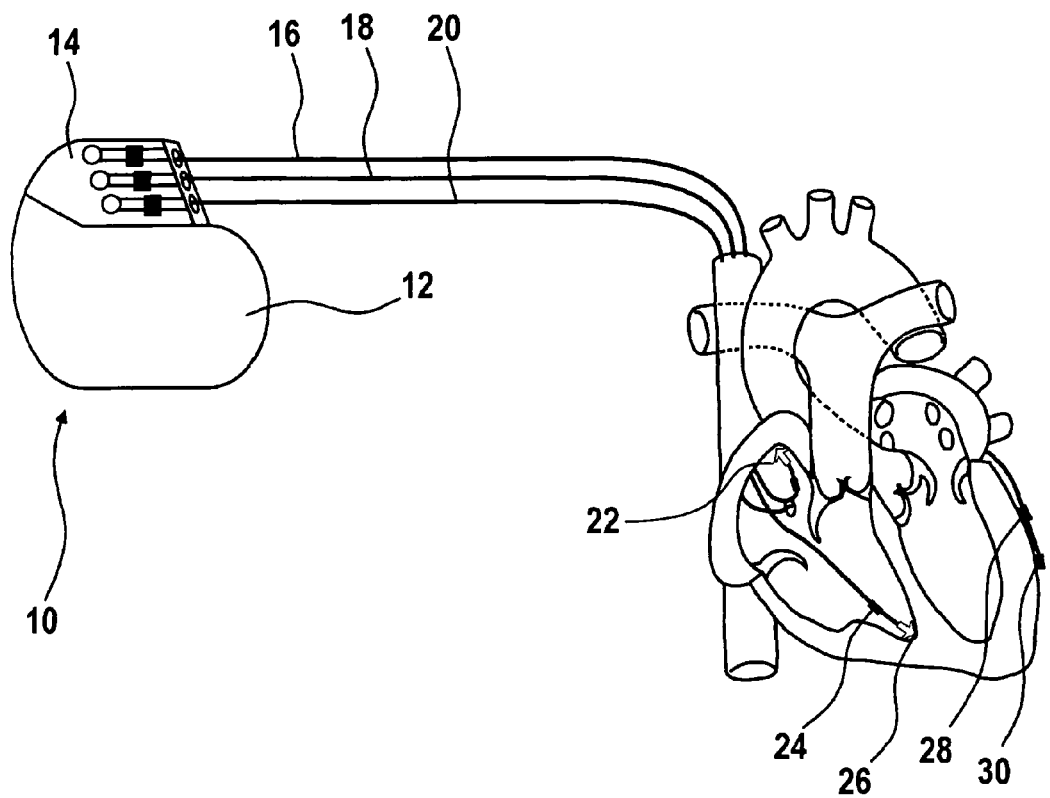
FIG. 1A shows a device according to the present invention in the form of a cardiac pacemaker together with electrodes connected thereto. The position of the electrodes in relation to a human heart is outlined.

FIG. 1A shows an implant 10, which is a cardiac pacemaker, for example. The implant 10 has a hermetically sealed metal housing 12 and a header 14 made of transparent plastic, which has multiple sockets for connecting electrode lines. The electrode line terminals in the header 14 are electrically connected to a control circuit in the interior of the housing of the cardiac pacemaker 10.

A total of three electrode lines are connected to the electrode line terminals, namely a right-atrial electrode line 16, a right-ventricular electrode line 18, and a left-ventricular electrode line 20.

The right-atrial electrode line 16 carries a right-atrial stimulation electrode 22. The right-ventricular electrode line 18 carries a right-ventricular ring electrode 24 and a right-ventricular tip electrode 26. The left-ventricular electrode line 20 is guided via the right atrium of the heart schematically shown in FIG. 1A and the coronary sinus of the heart up to the periphery of the left ventricle. The left-ventricular electrode line 20 carries a left-ventricular ring electrode 28 and a left-ventricular tip electrode 30.

For the impedance measurement of interest here, the implant 10 has an impedance measuring unit (see FIG. 2), which, in the preferred embodiment variation shown here (FIG. 2A), is connected for the purpose of impedance measurement to the right-ventricular ring electrode 24 and the right-ventricular tip electrode 26, as well as to the left-ventricular ring electrode 28 and the left-ventricular tip electrode 30.

Figure 1B:
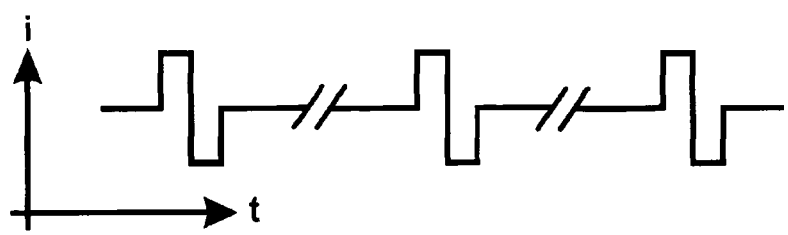
FIG. 1B shows an outline of the current fed for the impedance measurement.

A biphasic, pulsed measuring current, as it is outlined in FIG. 1B, is delivered via the right-ventricular ring electrode 24 and the right-ventricular tip electrode 26, i.e., in the right ventricle. The voltage caused by the current is measured via the left-ventricular ring electrode 28 and the left-ventricular tip electrode 30.

As may be seen from FIG. 1B, the current for impedance measurement is delivered in biphasic pulses, two constant current pulses in antiphase following one another directly and forming a pulse packet in each case. The individual pulse packets have a chronological spacing from one another, which is significantly greater than the duration of the particular pulse packet. The DC current pulses within the pulse packet each have identical strength, but with different polarity, and are each equally long. Typical values for the strength of the DC current pulses are between 50 μA and 600 μA. A typical pulse duration of a single current pulse is 15 μsec.

Figure 2A:
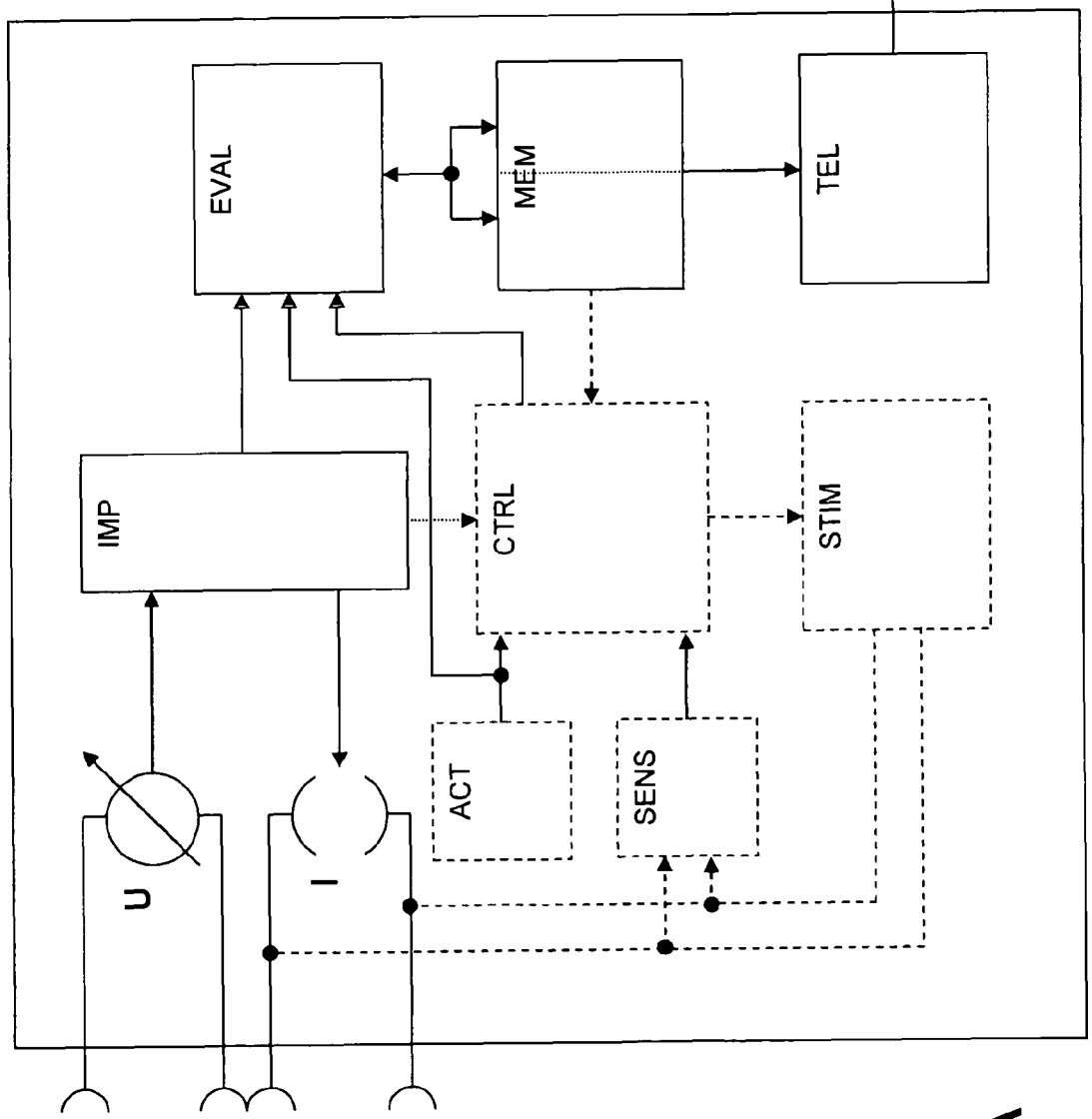
FIG. 2A shows a block diagram of essential components of the cardiac pacemaker from FIG. 1.
Figure 2B:
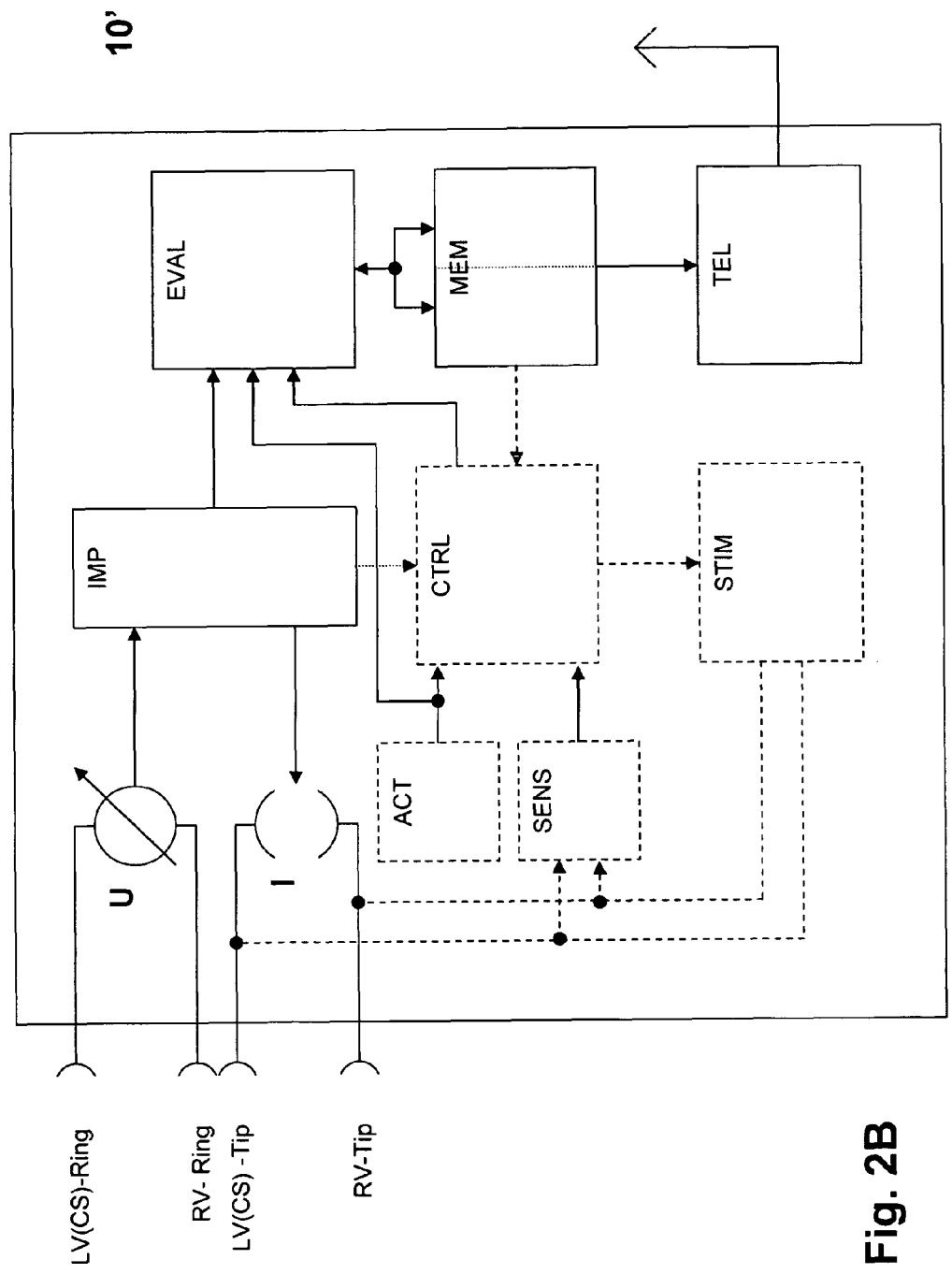
FIG. 2B shows a block diagram of essential components of the cardiac pacemaker from FIG. 1 in an embodiment variation alternative to FIG. 2A.

The spacing of the pulse packets from one another is, for example, 500 times greater than the duration of a current pulse. Notwithstanding the illustration in FIG. 1B, the two DC current pulses of a pulse packet may also follow one another with a chronological spacing, which corresponds to the duration of a DC current pulse. A gap of the duration of a DC current pulse, during which no DC current is delivered, then results between each two DC current pulses in antiphase of a pulse packet. A further variation is that the pulsed packets are delivered phase-alternating, i.e., a pulse packet begins with a negative DC current pulse and ends with a positive DC current pulse and the following pulse packet begins with a positive DC current pulse and ends with a negative DC current pulse and so forth, strictly alternately. Through this phase-alternating delivery of pulse packets, the load of the myocardium is reduced and artifacts are avoided. FIGS. 2A and 2B each show a block diagram having the essential components of a circuit in relation to the present invention in the interior of the housing 12 of the cardiac pacemaker 10. These components are an impedance measuring unit IMP, which is connected to a constant current generator I, which generates a pulsed, biphasic constant current, and delivers it via a terminal RV ring for the right-ventricular ring electrode 24 and a terminal RV tip for the right-ventricular tip electrode 26. In addition, the impedance measuring unit is connected to a voltage measuring unit U, which is in turn connected to two terminals, via which the particular voltage produced by the constant current delivered for impedance measuring purposes is detected. In the case of the preferred embodiment variation shown in FIG. 2A, the voltage measuring unit U is connected to a terminal LV ring for the left-ventricular ring electrode 28 and to a terminal LV tip for the left-ventricular tip electrode 30. In an alternative embodiment variation (see FIG. 2B), the voltage measuring unit U is connected to a terminal RV tip for the right-ventricular tip electrode 26, and, in addition, to a terminal LV tip for the left-ventricular tip electrode 30. In this embodiment variation, the current is fed via the right-ventricular ring electrode 24 at the terminal RV ring and the left-ventricular ring electrode 28 at the terminal LV ring.

The impedance measuring unit IMP is implemented to detect the curve of the intracardial impedance in time-sampled form and to relay a corresponding impedance curve signal to an analysis unit EVAL. The analysis unit EVAL is implemented to at least analyze the impedance curve during the diastole according to one of the variations described above.

Figure 3A:
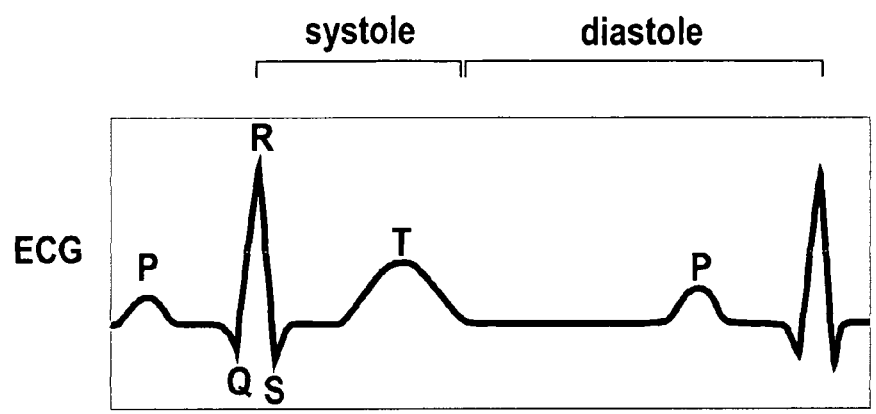
FIG. 3A shows an outline of an electrocardiogram over somewhat more than one cardiac cycle.
Figure 3B:
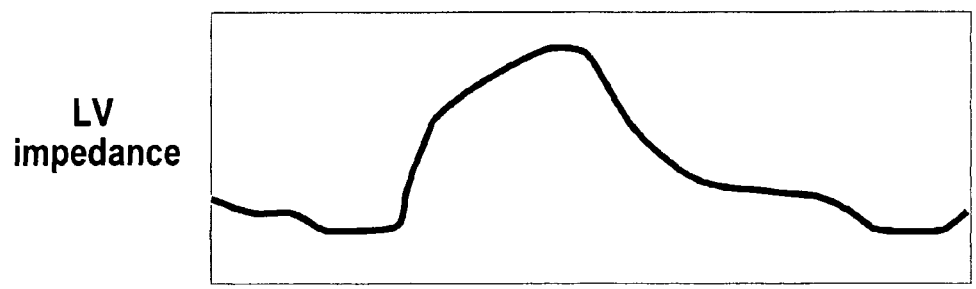
FIG. 3B shows a typical curve of the intracardial impedance in synoptic illustration to the curve of the electrocardiogram in FIG. 3A.
Figure 4:
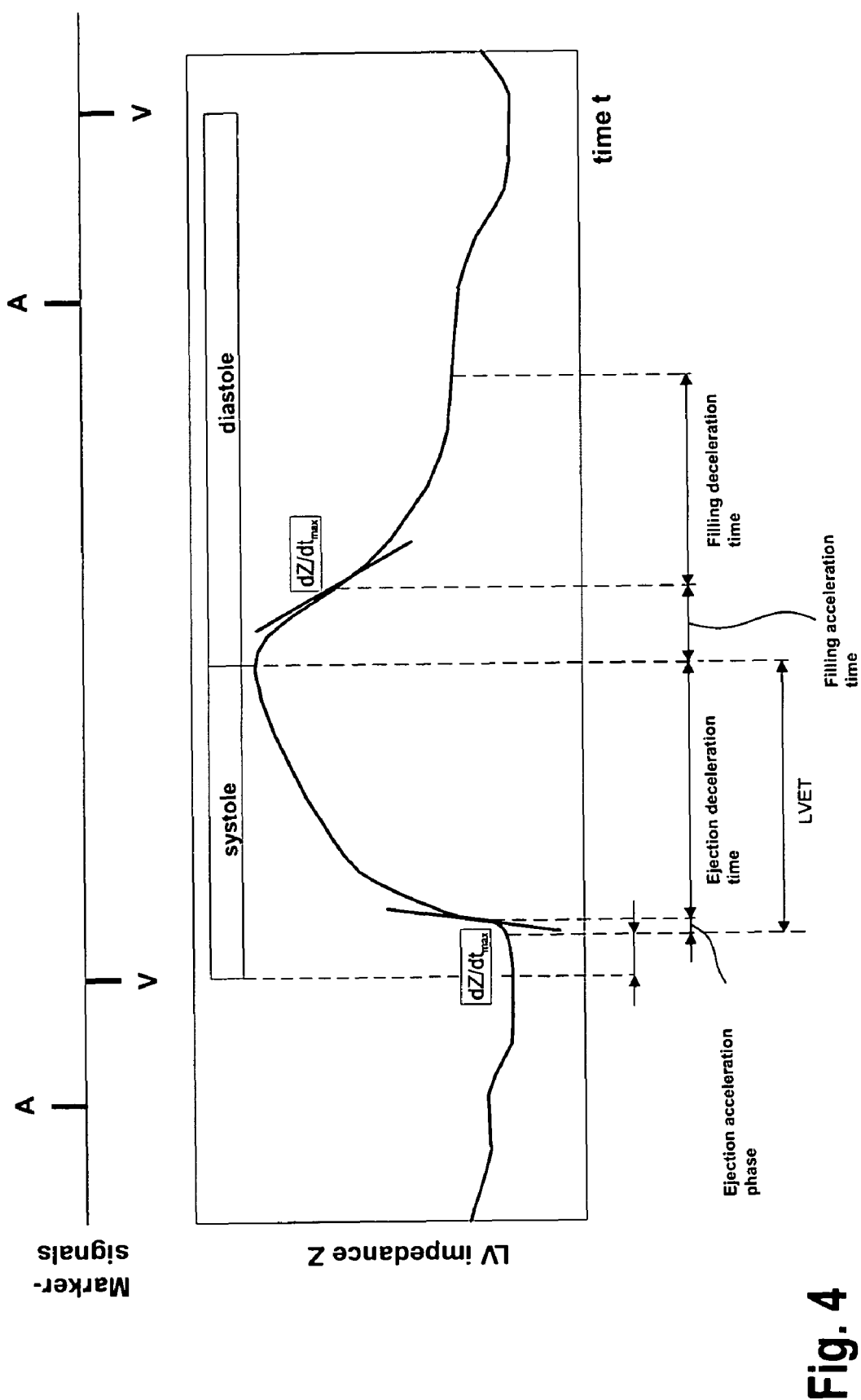
FIG. 4 shows a more differentiated illustration of the curve of the intracardial impedance to explain essential parameters related to the impedance curve.

A typical curve of the intracardial impedance is shown in FIG. 3B and FIG. 4. This impedance curve will be explained in connection with the description of these figures. In connection with FIG. 4, those instants of the slopes (gradients) of maxima and minima of the impedance curve which are used for determining the above-mentioned cardiac function parameters will be explained in particular.

In some cases, the impedance curve is advisably analyzed by the analysis unit with reference to a preferably intracardially detected electrocardiogram. This was already noted above, in particular with reference to the determination of the duration of the pre-ejection period (PEP). Known cardiac pacemakers already have corresponding sensing units SENS for detecting an intracardial electrocardiogram (iECG), which are connected to the terminal for the right-ventricular ring electrode 24 and the right-ventricular tip electrode 28, for example—as shown in the exemplary embodiment in FIGS. 2A and 2B. The intracardially detected electrocardiogram represents the electrical potentials which accompany the contraction and/or the expansion of the myocardium. A typical electrocardiogram curve is shown in FIG. 3A. In particular, the potentials which accompany a depolarization of the ventricular myocardium and thus a ventricular contraction may be seen from the electrocardiogram. These potentials may be inferred from the electrocardiogram as R waves. The repolarization of the myocardium and thus the beginning of the relaxation of the myocardium is coincident with the T wave in the electrocardiogram. A P wave characterizes the contraction of the atrium. Typically, cardiac pacemakers have a control unit CTRL, which is implemented to detect the instant of the occurrence of an R wave and a P wave and to generate a corresponding marker signal, which identifies a ventricular contraction (V) or an atrial contraction (A), respectively. The corresponding marker signals V and A identifying the instant of the occurrence of a R wave or a P wave, respectively, are also shown in FIGS. 4 and 5.

Furthermore, it may be seen from FIGS. 2A and 2B that the cardiac pacemaker 10 or 10' has an activity sensor ACT, which is typically used for the purpose of detecting phases of bodily activity of the patient. Bodily activity is typically accompanied by an increased metabolic demand, so that in known cardiac pacemakers, the detection of elevated bodily activity of the patient with the aid of the activity sensor ACT results in increase of the stimulation rate. In connection with the present invention, the output signal of the activity sensor ACT is additionally supplied to the analysis unit EVAL for the analysis of the impedance signal. The analysis unit EVAL uses the output signal of the activity sensor ACT to store ascertained cardiac function parameter values in one of the two memory areas of the memory MEM, depending on whether a cardiac function parameter value was detected during a phase of physical activity of the patient or during a rest phase of the patient.

Finally, the memory MEM is connected to a telemetry unit TEL, which contains at least one transmitter unit and is implemented for the purpose of transmitting data wirelessly from the memory MEM to a receiver outside the implant 10.

The connection between an electrocardiogram (ECG) and the curve of the left-ventricular impedance will now be explained briefly on the basis of FIGS. 3A and 3B. FIG. 3A shows a typical electrocardiogram and FIG. 3B shows a typical curve of the left-ventricular impedance in synoptic assignment to the electrocardiogram.

As noted, the electrocardiogram results from electrical potentials of the myocardium, as they occur together with the contraction and the relaxation of the myocardium. A contraction of the cardiac muscle tissue—the contraction of the left ventricle here—is triggered by an electrical potential (an electrical excitation), which results in depolarization of the cardiac muscle cells and, originating from an excitation location, propagates to the entire myocardium of a ventricle and thus results in contraction of the ventricle. These electrical potentials resulting in depolarization of the cardiac muscle cells and thus contraction of the cardiac tissue may be recognized in the electrocardiogram as R waves. The repolarization of the cardiac tissue, which accompanies the relaxation of the myocardium, is coincident with the T waves recognizable in the electrocardiogram. A P wave results from the electrical potentials which accompany the contraction of the atrium.

As may be seen from the curve of the left-ventricular impedance in FIG. 3B, the impedance has a minimum approximately at the instant of the occurrence of the R wave. At this instant, the ventricle has its greatest volume and therefore has the lowest impedance. The ventricle begins to contract with a slight delay after the occurrence of the R wave, so that the impedance increases until it reaches its maximum when the ventricle is maximally contracted. The phase of the rise of the left-ventricular impedance accompanies the ejection phase (systole) of the heart, in which blood is pressed out of the ventricle through the aortal flap into the aorta. After the ventricle has reached its maximally contracted state, the cardiac muscle tissue (myocardium) repolarizes. The beginning of the repolarization may be recognized in the electrocardiogram as a T wave and results in the left-ventricular impedance falling again after reaching the impedance maximum. The drop of the left-ventricular impedance reflects the volume of the left ventricle, which enlarges with increasing relaxation of the myocardium. A contraction of the atrium, which precedes a P wave in the electrocardiogram, results in further filling of the ventricle and a corresponding volume enlargement and thus a further impedance drop until finally a renewed contraction of the ventricle occurs.

Finally, the instants and values which the analysis unit ascertains to determine the cardiac function parameter values are shown in FIG. 4. Most of the cardiac function parameters whose values the analysis unit is implemented to determine are also plotted in FIG. 4.

In addition, it is indicated in FIG. 4 that the analysis unit EVAL assigns values and instants to be inferred from the impedance curve to the instants of the occurrence of an R wave and a P wave in the electrocardiogram by analyzing corresponding marker signals V and A.

It may be inferred from FIG. 4 that the systole, i.e., the ejection phase, extends from the instant of the depolarization of the ventricular myocardium, characterized by a V marker—until reaching the minimum ventricular chamber volume—characterized by the maximum of the impedance curve. The diastole, which is especially of interest in connection with the present invention, extends in time from the instant of the occurrence of the impedance maximum up to the next ventricular depolarization.

The pre-ejection phase PEP extends from the beginning of the ventricular depolarization (V marker) up to the clear beginning of an impedance increase. The ejection acceleration phase extends from this clear rise of the left-ventricular impedance up to reaching the instant in which the impedance curve has its greatest positive slope, i.e., the gradient of the impedance curve is greatest. The ejection deceleration time extends from the instant of the occurrence of the maximum slope (maximum gradient) of the impedance curve until reaching the impedance maximum. Ejection acceleration time and ejection deceleration time, taken together, result in the left-ventricular ejection time (LVET). Upon reaching the maximum left-ventricular impedance, the ejection phase of the heart, i.e., the systole, ends and the filling phase, i.e., the diastole, begins.

The diastole begins with the filling acceleration time, which extends in time from the occurrence of the maximum of the impedance curve up to the instant of the occurrence of the maximum negative slope of the impedance curve (maximum negative gradient dZ/dtMin). The filling deceleration time begins with the instant of the occurrence of the maximum negative gradient and extends up to the occurrence of the apex of a parabolic approximation function of the impedance curve, beginning with the instant of the occurrence of the maximum negative slope.

The determination of the alternation of a cardiac function parameter by the analysis unit EVAL, which was already noted, will now be explained with reference to FIGS. 5A and 5B.

FIG. 5A shows a typical, alternating impedance curve over multiple cycles in chronological relation to the occurrence of atrial and ventricular events (depolarizations), characterized by A markers and V markers.

The particular ejection acceleration time is plotted as a second cardiac function parameter which may be derived from the left-ventricular impedance in FIG. 5A.

The values for the maximum gradient of the impedance curve and for the ejection acceleration time for each of the cardiac cycles shown are plotted in the diagram in FIG. 5B. It may be recognized clearly that both cardiac function parameters alternate from cardiac cycle to cardiac cycle. A look at FIG. 5A shows that a corresponding alternation may also be recognized in relation to the maximum amplitude value of the impedance curve.

It results that in the example shown in FIG. 5A, different cardiac function parameters alternate in an ABAB pattern.

The analysis unit EVAL is implemented to detect such an alternation for one or more of the cardiac function parameters detected by the analysis unit EVAL. To ascertain an alternation and/or a variability of the cardiac function parameter of this type, the analysis unit is implemented to perform the change of the cardiac function parameters in the time or frequency ranges. Determining the alternation and the variability may be performed for one or more of the cardiac function parameters.

The analysis unit EVAL may derive different risk marker signals from the alternations and variabilities thus ascertained. Such risk marker signals may, for example, be used as short-term predictors for life-threatening cardiac arrhythmias, since alternations or variabilities of cardiac function parameter values derived from the impedance may be precursors of a ventricular fibrillation. The prediction of a ventricular fibrillation goes back to the analysis of a few more recent cardiac cycles, i.e., it represents a short-term analysis. A long-term analysis of the risk parameters may be used for predicting the risk of sudden cardiac death or for observing the course of a cardiac illness such as severe congestive heart failure.

Furthermore, the analysis unit EVAL may be implemented to optimize electrotherapy by the cardiac pacemaker 10, i.e., in particular to set the parameters decisive for the electrical stimulation of the heart, such as the instant and strength of stimulation pulses, as a function of the cardiac function parameter values ascertained by the analysis unit EVAL. The treatment parameters optimized in this way include the stimulation rate and the atrioventricular deceleration time. In two-chamber pacemakers (biventricular pacemakers), the analysis unit may also be implemented to optimize the intraventricular deceleration time or the biventricular stimulation mode on the basis of the cardiac function parameter values derived from the impedance. In regard to the biventricular stimulation mode, the analysis unit determines whether the stimulation is to be performed only in the left ventricle, only in the right ventricle, or whether a stimulation of both ventricles is to be performed as a function of which stimulation form results in the greatest value of the maximum of the gradient of the impedance curve during the systole. The analysis unit also optimizes the intraventricular deceleration time in the same way.

In an analogous way, the cardiac function parameter values ascertained by the analysis unit EVAL may also be analyzed to optimize a medication treatment.

What is claimed is:

1. A device for detecting the state of a heart on the basis of intracardial impedance measurement comprising:
   at least two electrodes;
   an impedance measuring unit which is electrically connected to the at least two electrodes;
   wherein said impedance measuring unit is configured to deliver a delivered current or apply an applied voltage and detect a voltage or a current;
   wherein said impedance measuring unit is configured to ascertain an impedance based on a quantity of said delivered current or said applied voltage and a voltage drop caused by the current, or the current caused by the voltage and derive an impedance curve;
   an analysis unit, connected to said impedance measuring unit and configured to identify a diastole in said impedance curve as a period between maximum and minimum impedance, and to derive a maximum negative gradient of the impedance curve during said diastole; and,
   wherein said analysis unit is configured to determine a period of time between a beginning of an impedance reduction in said impedance ascertained by said impedance measuring unit and a following occurrence of the maximum negative gradient of said impedance curve derived by said impedance measuring unit as a cardiac function parameter through analysis of said impedance curve.

2. The device according to claim 1 wherein said analysis unit is configured to determine either a period of time between an occurrence of the maximum negative gradient and an apex of a parabolic approximation function of said impedance curve, beginning with said occurrence of said maximum negative gradient, or a time constant of a next potential approximation function of said impedance curve, beginning with said occurrence of said maximum negative gradient, as a value of the cardiac function parameter, namely a filling deceleration time, through analysis of said impedance curve.

3. The device according to claim 1 wherein said analysis unit is configured to determine a ratio of the maximum negative gradient of said impedance curve between the beginning of the impedance reduction and a following atrial contraction to said maximum negative gradient of the impedance curve between this atrial contraction and a following further increase of said impedance curve as a value of the cardiac function parameter through analysis of said impedance curve.

4. The device according to claim 1 wherein said analysis unit is configured to determine a duration of a particular diastole as the cardiac function parameter value through analysis of said impedance curve, in that said analysis unit determines a period of time between the beginning of the impedance reduction after exceeding the maximum impedance and an occurrence of the minimum impedance of said impedance curve, through analysis of said impedance curve.

5. The device according to claim 1 wherein said analysis unit is configured to analyze said impedance curve assigned to a systole and to calculate the cardiac function parameter value that characterizes behavior of a heart during said systole or ejection phase of a ventricle or contraction.

6. The device according to claim 5 wherein said analysis unit is configured to determine a positive maximum of a gradient of said impedance curve as the cardiac function parameter value.

7. The device according to claim 5 wherein said analysis unit is configured to determine a maximum of a product of a slope of a gradient of said impedance curve and a gradient of said impedance curve as the cardiac function parameter value.

8. The device according to claim 5 wherein said analysis unit is configured to determine a period of time of a pre-ejection phase as the cardiac function parameter value, in that said analysis unit determines said period of time between an electrical activation of ventricular myocardium and a beginning of an impedance increase, through analysis of said impedance curve.

9. The device according to claim 5 wherein said analysis unit is configured to determine a period of time of a left-ventricular ejection time, in that said analysis unit determines said period of time between a beginning of impedance increase and a maximum of said impedance curve, through analysis of said impedance curve.

10. The device according to claim 5 wherein said analysis unit is configured to determine a period of time between a beginning of impedance increase and a following occurrence of a maximum gradient of said impedance curve as a value of the cardiac function parameter, namely an ejection acceleration time, through analysis of said impedance curve.

11. The device according to claim 5 wherein said analysis unit is configured to determine a period of time between an occurrence of a maximum gradient of said impedance curve and a maximum of said impedance curve as a value of the cardiac function parameter, namely an ejection deceleration time, through analysis of impedance curve.

12. The device according to claim 10 wherein said analysis unit is configured to determine a period of time between an occurrence of a maximum gradient of said impedance curve and a maximum of said impedance curve as a value of the cardiac function parameter, namely an ejection deceleration time, through analysis of impedance curve and is further configured to calculate a ratio of ejection acceleration time to ejection deceleration time for a particular cardiac cycle.

13. The device according to claim 1 further comprising a memory, connected to said analysis unit and which is configured to store cardiac function parameter values ascertained by said analysis unit.

14. The device according to claim 13 further comprising:
an activity detection unit;
wherein said analysis unit is coupled with the activity detection unit, which is configured to detect states of physical activity of a patient and rest states of said patient in a differentiated way and to generate a corresponding activity or rest output signal, said memory having at least two memory areas, of which a first memory area is provided to store cardiac function parameter values which were detected during a phase of physical activity of said patient and a second memory area to store cardiac function parameter values which were detected during a rest phase of said patient, wherein said analysis unit is configured to store cardiac function parameter values in said first memory area or said second memory area as a function of said activity or rest output signal of said activity detection unit.

15. The device according to claim 14 wherein said activity detection unit is configured to differentiate multiple states of physical activity of different intensities, wherein said memory has multiple memory areas, and said analysis unit is configured to store cardiac function parameter values in one of said multiple memory areas depending on an intensity of an assigned physical activity as a function of said activity or rest output signal of said activity detection unit.

16. The device according to claim 15 wherein said analysis unit is configured to calculate mean values of cardiac function parameter values of the cardiac function parameter over a predefined period of time.

17. The device according to claim 15 wherein said analysis unit is configured to detect an alternation of the cardiac function parameter from cardiac cycle to cardiac cycle.

18. The device according to claim 15 further comprising a telemetry unit, which comprises at least one transmitter for wireless transmission of data wherein said telemetry unit is connected to said memory.

19. The device according to claim 1 further comprising an electrostimulation device coupled with said at least two electrodes.

20. The device according to claim 19 wherein said device is implantable.

21. The device according to claim 18 wherein said device is an implantable cardiac pacemaker or cardioverter/defibrillator or both.

* * * * *